US012089665B2

(12) United States Patent
Driessen

(10) Patent No.: US 12,089,665 B2
(45) Date of Patent: Sep. 17, 2024

(54) SAFETY GARMENT WITH INTEGRATED EARPLUGS

(71) Applicant: Peter Driessen, Loveland, CO (US)

(72) Inventor: Peter Driessen, Loveland, CO (US)

( * ) Notice: Subject to any disclaimer, the term of this patent is extended or adjusted under 35 U.S.C. 154(b) by 0 days.

(21) Appl. No.: 18/339,364

(22) Filed: Jun. 22, 2023

(65) Prior Publication Data
US 2023/0329367 A1 Oct. 19, 2023

Related U.S. Application Data

(62) Division of application No. 16/247,100, filed on Jan. 14, 2019, now Pat. No. 11,717,037.

(60) Provisional application No. 62/680,052, filed on Jun. 4, 2018.

(51) Int. Cl.
| | | |
|---|---|---|
| *A41D 13/01* | (2006.01) | |
| *A41D 1/04* | (2006.01) | |
| *A41D 27/08* | (2006.01) | |
| *A61F 11/08* | (2006.01) | |

(52) U.S. Cl.
CPC ............ *A41D 13/01* (2013.01); *A41D 1/04* (2013.01); *A41D 27/08* (2013.01); *A61F 11/08* (2013.01); *A41D 2200/20* (2013.01); *A41D 2300/22* (2013.01); *A41D 2300/332* (2013.01); *A41D 2600/20* (2013.01)

(58) Field of Classification Search
CPC .......... A41D 13/01; A41D 1/04; A41D 27/08; A61F 11/08
See application file for complete search history.

(56) References Cited

U.S. PATENT DOCUMENTS

| | | | |
|---|---|---|---|
| 2,487,038 A | 11/1949 | Jasper | |
| 3,810,804 A * | 5/1974 | Rowland | B29D 11/00605 |
| | | | 359/530 |
| 4,461,290 A | 7/1984 | Gardner et al. | |
| 5,074,375 A | 12/1991 | Grozil | |
| 5,159,718 A | 11/1992 | Moyer | |
| 5,193,226 A | 3/1993 | Mortenson | |
| 5,475,449 A | 12/1995 | Pyle | |
| 5,581,821 A | 12/1996 | Nakano | |
| 5,781,272 A | 7/1998 | Bright et al. | |
| 5,809,574 A | 9/1998 | Falco et al. | |

(Continued)

FOREIGN PATENT DOCUMENTS

WO 2010090535 A2 8/2010

*Primary Examiner* — Alissa L Hoey
(74) *Attorney, Agent, or Firm* — Boudwin Intellectual Property Law, LLC; Daniel Boudwin

(57) ABSTRACT

A safety garment with integrated earplugs designed to provide both hearing protection and high-visibility in a single garment. The safety garment with integrated earplugs includes a garment, such as a vest or sweatshirt, designed to enclose a user's torso, with a neck aperture along a top end designed to receive a head and neck therethrough and a pair of arm apertures on opposing sides, with each arm aperture designed to receive an arm therethrough. A reflective material is disposed along an exterior surface of the garment, such that the garment qualifies as a high-visibility safety garment. Additionally, a cord having a pair of opposing ends is affixed to the garment and an earplug is affixed to each end of the cord. In this way, a user is able to wear a single garment that provides both high visibility to the user and has hearing protection attached.

5 Claims, 3 Drawing Sheets

(56) References Cited

U.S. PATENT DOCUMENTS

| | | |
|---|---|---|
| 5,887,070 A | 3/1999 | Iseberg et al. |
| 6,128,783 A | 10/2000 | Blauer et al. |
| 6,148,442 A | 11/2000 | Porter |
| 6,286,622 B1 | 9/2001 | Tiemann |
| 6,382,213 B1 | 5/2002 | Sanpei |
| 6,477,711 B1 | 11/2002 | Freeman et al. |
| RE40,696 E | 4/2009 | Iseberg et al. |
| 7,519,192 B1 | 4/2009 | Laycock et al. |
| 7,784,583 B1 | 8/2010 | Hall et al. |
| 7,991,179 B2 | 8/2011 | Drambarean et al. |
| 8,333,260 B1 | 12/2012 | Hall et al. |
| 8,638,970 B2 | 1/2014 | Burton |
| D742,099 S | 11/2015 | Wager |
| 9,242,093 B1 | 1/2016 | Sherman |
| 9,282,390 B1 | 3/2016 | Turdjian |
| D768,938 S | 10/2016 | Bien et al. |
| 9,814,300 B2 | 11/2017 | Webster |
| 10,240,773 B1 | 3/2019 | Francis et al. |
| 10,368,593 B2 * | 8/2019 | Romo .................. A41D 27/20 |
| D874,157 S | 2/2020 | Tutor |
| 10,893,715 B2 | 1/2021 | Noll |
| 10,925,340 B2 | 2/2021 | Brandt et al. |
| D924,488 S | 7/2021 | Driessen |
| 11,717,037 B2 * | 8/2023 | Driessen ................ A41D 1/04 2/84 |
| 2004/0143882 A1 | 7/2004 | Gardner et al. |
| 2005/0141743 A1 | 6/2005 | Seto |
| 2005/0230181 A1 | 10/2005 | Woo |
| 2006/0000003 A1 | 1/2006 | Grilliot et al. |
| 2006/0026731 A1 | 2/2006 | Qashou |
| 2006/0261113 A1 | 11/2006 | Godshaw et al. |
| 2008/0005825 A1 | 1/2008 | Tronvold |
| 2008/0030856 A1 | 2/2008 | King |
| 2008/0187159 A1 | 8/2008 | Blanchard |
| 2009/0199322 A1 | 8/2009 | Parrish |
| 2009/0199326 A1 | 8/2009 | Brauner et al. |
| 2009/0235426 A1 | 9/2009 | Johnston et al. |
| 2011/0019861 A1 | 1/2011 | Wolfe |
| 2011/0129110 A1 | 6/2011 | Wolfe |
| 2012/0243724 A1 | 9/2012 | Takai et al. |
| 2013/0031695 A1 | 2/2013 | Roemer et al. |
| 2013/0044908 A1 | 2/2013 | Gotlieb |
| 2013/0130540 A1 | 5/2013 | Oman et al. |
| 2013/0152270 A1 | 6/2013 | Neal et al. |
| 2014/0047614 A1 | 2/2014 | Becton |
| 2014/0140568 A1 | 5/2014 | Im et al. |
| 2014/0317829 A1 | 10/2014 | Rolfe |
| 2015/0000016 A1 | 1/2015 | Crawford et al. |
| 2015/0196061 A1 | 7/2015 | Oliver |
| 2016/0015104 A1 | 1/2016 | Edwards et al. |
| 2016/0198781 A1 | 7/2016 | Israel et al. |
| 2016/0286943 A1 | 10/2016 | Andersen et al. |
| 2018/0116300 A1 | 5/2018 | Fleming |
| 2018/0250168 A1 | 9/2018 | Herring et al. |
| 2019/0261718 A1 | 8/2019 | O'Connor et al. |
| 2019/0274416 A1 * | 9/2019 | Paillasson ................ A44B 1/18 |
| 2020/0085118 A1 | 3/2020 | Fella |
| 2020/0179173 A1 | 6/2020 | Brown et al. |
| 2020/0268088 A1 | 8/2020 | Sanchez |
| 2020/0315269 A1 | 10/2020 | Roberts |

* cited by examiner

SAFETY GARMENT WITH INTEGRATED EARPLUGS

CROSS REFERENCE TO RELATED APPLICATIONS

This application claims the benefit of U.S. Non-Provisional application Ser. No. 16/247,100 filed on Jan. 14, 2019 and U.S. Provisional Application No. 62/680,052 filed on Jun. 4, 2018. The above identified patent application is herein incorporated by reference in its entirety to provide continuity of disclosure.

BACKGROUND OF THE INVENTION

The present invention relates to safety garments. More specifically, the invention provides a safety garment with integrated earplugs having a garment configured to be worn with a reflective material disposed on the exterior surface, having a cord with an earplug on either end affixed to the garment.

Many people who work in noisy workplaces, such as construction or manufacturing, suffer from hearing loss due to repeated and prolonged exposure to the loud noises produced by industrial machines and work tools. Although these workers wear earplugs to mitigate the hearing loss, traditional earplugs are typically lost or misplaced, often leaving these workers without a means of hearing protection. Additionally, earplugs stored in the pockets of the individual will often become dirty or damaged. Thus, a device that is configured to enable a user to wear a single garment that provides both high visibility to the user and has hearing protection attached is desired.

SUMMARY OF THE INVENTION

In view of the foregoing disadvantages inherent in the known types of safety garments now present in the known art, the present invention provides a safety garment with integrated earplugs wherein the same can be utilized for providing convenience for the user when desiring a single garment that qualifies as a high-visibility safety garment and has hearing protection attached to the garment.

The present system comprises a safety garment with integrated earplugs. The safety garment with integrated earplugs comprises a garment configured to encircle a user's torso, having a neck aperture along a top end configured to receive a head and neck therethrough and a pair of arm apertures disposed on opposing sides, wherein each arm aperture is configured to receive an arm therethrough. A reflective material is disposed along a portion of an exterior surface of the garment, such that the garment qualifies as a high-visibility safety garment. Additionally, a cord having a pair of opposing ends is affixed to the garment, wherein an earplug is affixed to each end of the cord. In this way, a user is able to wear a single garment that provides both high visibility to the user and has hearing protection affixed thereto.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
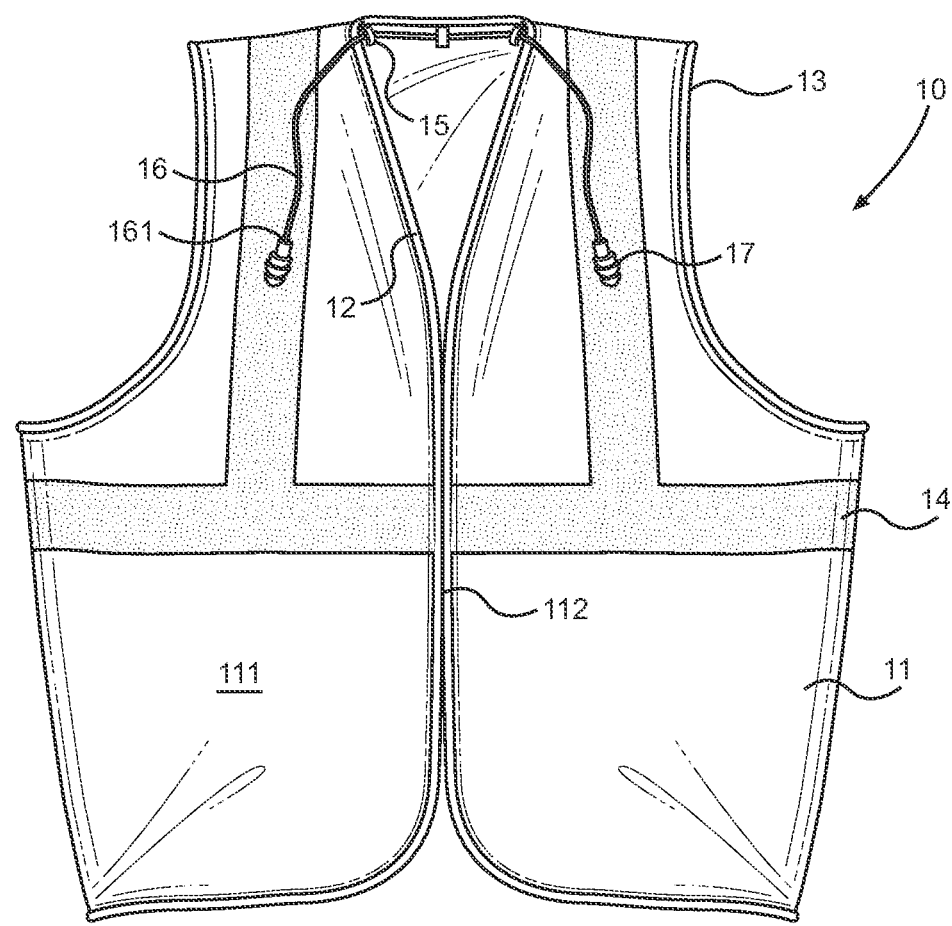
FIG. 1 shows a perspective view of an embodiment of the safety garment with integrated earplugs.

Reference is made herein to the attached drawings. Like reference numerals are used throughout the drawings to depict like or similar elements of the safety garment with integrated earplugs. The figures are intended for representative purposes only and should not be considered to be limiting in any respect.

Referring now to FIG. 1, there is shown a perspective view of an embodiment of the safety garment with integrated earplugs. The safety garment with integrated earplugs 10 comprises a garment 11 configured to encircle a user's torso, wherein the garment 11 is traditionally manufactured, such that the garment 11 includes a neck aperture 12 configured to receive a head and neck of an individual therethrough, and a pair of arm apertures 13, wherein each arm aperture 13 is configured to receive an arm of an individual therethrough. As the safety garment with integrated earplugs 10 is configured to be worn by an individual, the garment 11 is sized to encompass a torso of the individual, and as such, specific measurements will vary.

A reflective material 14 is disposed on an exterior surface 111 of the garment 11. The reflective material 14 is configured to be highly reflective, such that the reflective material 14 reflects back at least 50% of incoming light. In this way, the garment 11 and the individual wearing the garment 11 are easily distinguishable from the surrounding area, thereby enhancing the safety of the individual. In the illustrated embodiment, the reflective material 14 comprises a metallic coating, such as powdered aluminum on an uppermost layer. However, in other embodiments, any material having highly reflective properties can be used for the reflective material 14.

In the shown embodiment, the reflective material 14 is permanently affixed to the exterior surface 111, such as via sewing the reflective material 14 into the garment 11 or onto the exterior surface 111. However, in other embodiments, the reflective material 14 is permanently secured to the exterior surface 111 through other means, such as via adhesive tape or other suitably secure means. In the illustrated embodiment, the reflective material 14 is disposed along the exterior surface 111 in several contiguous sections. The reflective material 14 is disposed parallel to a bottom edge of the garment 11, such that the reflective material 14 is positioned annularly about the torso. Additionally, the reflective material 14 is disposed parallel to each arm aperture 13, such that the reflective material 14 is positioned across each shoulder of the user and adjoining the reflective material 14 disposed around the torso. In this way, the reflective material 14 is disposed about the garment 11 such that the reflective material 14 can be seen regardless of the angle from which the individual is seen.

In the illustrated embodiment, the garment 11 is configured to resemble a vest, such that the garment 11 includes a split 112 along the exterior surface 111, extending linearly from the neck aperture 12 to a distal point along the bottom edge of the garment 11. The split 112 is oriented parallel to the arm apertures 13 and is positioned along a central axis, as is standard for a conventional vest. The split 112 allows the user to swiftly transfer into areas requiring high visibility clothing by aiding them in quickly donning or discarding the garment 11 as necessary. In one embodiment, a clothing fastener is disposed on an interior of the vest along the split 112 such that a user can secure the garment 11 in a closed position.

A cord 16 is affixed to the garment 11, wherein the cord 16 has a pair of opposing ends. The cord 16 comprises a length such that each end is dimensioned to reach each ear of the user. In the shown embodiment, the cord 16 is permanently affixed to the garment 11, thereby preventing the user from accidentally misplacing the cord 16. The cord 16 is composed of any durable rope-like material, such as nylon or twine. In some embodiments, the cord 16 has elastic properties, such that the cord 16 can be stretched to a desired length when pulled and return to a shortened length when no longer required, thereby preventing the cord 16 from becoming tangled, as is common with cords over a certain length. In the illustrated embodiment, the cord 16 is disposed along a perimeter of the neck aperture 12, such that the cord 16 hangs over the user's shoulders within reach when not in use.

In the shown embodiment, the cord 16 is secured about the neck aperture 12 via a plurality of loops 15 configured to receive the cord 16 therethrough. Each loop 15 is permanently secured to the neck aperture 12 of the garment 11 through a means of fastening, such as sewing. Additionally, each loop 15 is aligned with one another along an axis extending around the perimeter of the neck aperture 12. The cord 16 is disposed in the space between the loop 15 and the garment 11, thereby securing the cord 16 to the garment 11. The space between the plurality of loops 15 and the garment 11 create a channel for the cord 16 to move through, thereby allowing the user to manipulate the cord 16 therethrough to adjust a length on either side of the user's torso without allowing the opposing ends thereof to pass therethrough.

An earplug 17 is affixed to each end of the cord 16, thereby allowing the user to plug their ears in an environment with a great deal of noise. In the illustrated embodiment, each earplug 17 is permanently affixed to each end, thereby allowing the user to quickly place the earplug 17 into their ear and preventing the user from losing the earplug 17. In the shown embodiment, the earplug 17 is composed of a foam material, such that the earplug 17 conforms to the inner contours of the user's ears.

Figure 2:
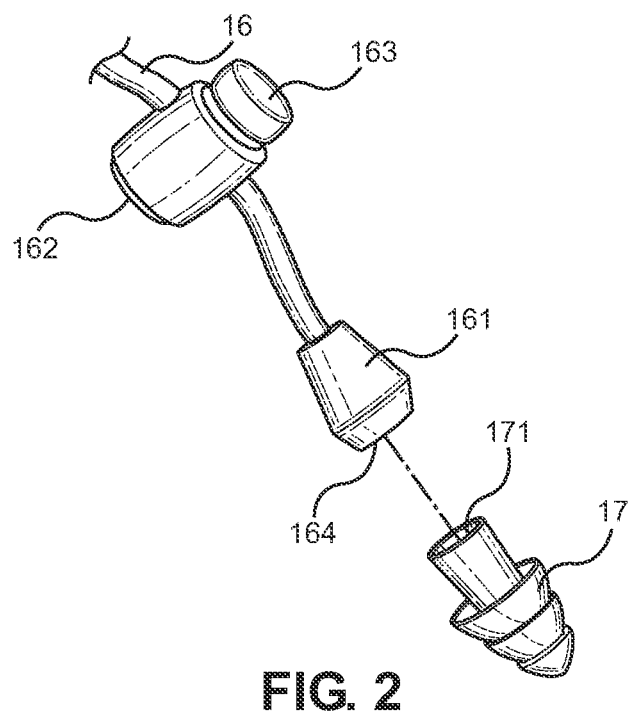
FIG. 2 shows a close-up perspective view of an embodiment of the earplugs.

Referring now to FIG. 2, there is shown a close-up perspective view of an embodiment of the earplugs. In the illustrated embodiment, the cord 16 is fed through a cord lock 162, such that the cord 16 is configured to act as a drawstring. The cord lock 162 is configured to restrict an amount of the cord 16 within the channel, thereby decreasing the circumference of the hood aperture. The cord lock 162 comprises a standard model, such that the cord lock 162 includes a plunger 163 on a first end thereof. The plunger 163 is in communication with a spring 165 disposed within a barrel of the cord lock 162, wherein the cord 16 is disposed within the plunger 163. In this way, the spring 165 provides a tension on the plunger 163 to force the plunger 163 into a raised position, thereby preventing the cord 16 from sliding through the cord lock 162. Thus, when the plunger 163 is depressed, the tension on the spring 165 is released, thereby allowing the cord lock 162 to move freely along the cord 16. In this way, the cord 16 can retained in a tightened condition or released, depending on the user's desire.

In the illustrated embodiment, the plunger 163 includes a planar top opposite the spring, such that the planar top of the plunger 163 is disposed outside the barrel of the cord lock 162. In this way, the planar top of the plunger 163 functions as an indication of where the user should depress the plunger 163, thereby aiding them in operating the cord lock 162 and drawstring mechanism of the cord 16.

In the shown embodiment, each end of the cord 16 comprises a fastener 161 configured to secure to the earplug 17. In the illustrated embodiment, each earplug 17 is removably securable to the cord 16 through the fastener 161 disposed at each end. In this way, the user can easily change the earplug 17 should they desire a different type of earplug, or if the earplug 17 becomes lost or damaged. In the shown embodiment, the fastener 161 comprises a plastic shell having an aperture 164 at a distal end thereof configured to receive the earplug 17 therein. The earplug 17 comprises a fitted end 171 opposite a plurality of conical members 172, wherein the fitted end 171 is configured to removably secure into the aperture 164 of the fastener 161 and the plurality of conical members 172 are configured to fit a variety of ear canal sizes while providing sound insulation.

In the shown embodiment, the earplug 17 is configured to frictionally secure within the fastener 161, such that the user can quickly slide the earplug 17 out of the fastener 161. However, in other embodiments, the earplug 17 includes a hook and loop, clip, or spring-biased fastener at the fitted end 171, or any other suitably secure type fastener. In this way, the fastener 161 allows for a release mechanism safety feature wherein the earplugs 17 are quickly and harmlessly removed from the fastener 161 should the cord 16 become trapped, thereby preventing movement.

Figure 3:
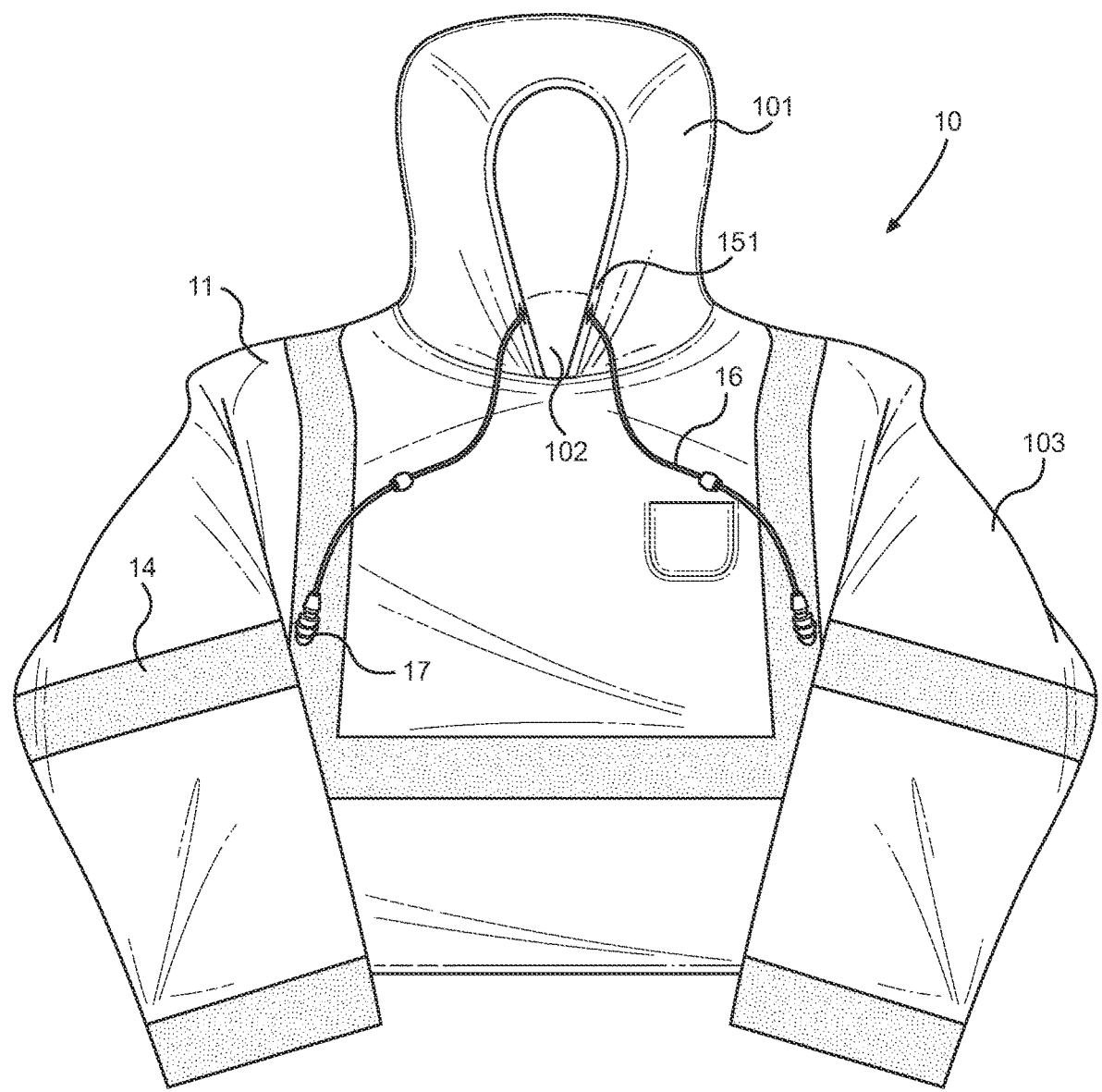
FIG. 3 shows a perspective view of another embodiment of the safety garment with integrated earplugs.

Referring now to FIG. 3, there is shown a perspective view of another embodiment of the safety garment with integrated earplugs. In the illustrated embodiment, the safety garment with integrated earplugs 10 includes a hood 101 affixed to the neck aperture of the garment 11, wherein the hood 101 includes a hood aperture 102 configured to receive the neck and head therethrough such that the user is able to removably cover their head using the hood 101 while retaining their central vision.

In the illustrated embodiment, the hood aperture 102 includes a channel 151 disposed about a perimeter thereof, having two openings disposed opposite one another. The channel 151 is configured to receive the cord 16 therethrough, such that each earplug 17 is disposed through an opening of the channel 151. In this way, the drawstring mechanism of the cord 16 allows the user to restrict the channel 151, thereby decreasing the circumference of the hood aperture 102 allowing the user to secure the hood 101 around their face.

Further, the safety garment with integrated earplugs 10 includes a pair of sleeves 103 having a length equivalent to one another, wherein each sleeve 103 is permanently affixed to each arm aperture of the garment 11. In the illustrated embodiment, each sleeve 103 is dimensioned to encompass the entire arm of the user, such that the length of the sleeve 103 and the length of the arm are equivalent. However, in other embodiments each sleeve 103 has a length less than the length of the arm of the user, such that the garment 11 is short sleeved.

Additionally, in the shown embodiment the garment 11 includes at least one pocket 30 disposed on the exterior surface thereof. The pocket 30 allows the user to store their earplugs 17 therein when removed from the cord 16. In the illustrated embodiment, the pocket 30 is disposed on a front surface of the garment 11, aligned with a breast pocket of a user. However, in other embodiments, the pocket 30 is disposed along one or more sleeves 103. In an additional embodiment, the pocket 30 further includes a pocket fastener, such that items stored therein can be secured.

In the illustrated embodiment, the reflective material 14 is disposed about the torso of the garment 11 and is additionally disposed along each sleeve 103. In the shown embodiment, the reflective material 14 is disposed about a circumference of each sleeve at an end of the sleeve 103 and at a midpoint of the sleeve 103, such that the reflective material is oriented parallel to the arm aperture of the sleeve 103. Thus, the reflective material 14 is visible along the arm of the user regardless of how the arm is manipulated. In this way, when the user is wearing the garment 11 as illustrated in the embodiment shown in FIG. 3, they are still provided the protection associated with the high-visibility qualities of the reflective material 14.

Figure 4:
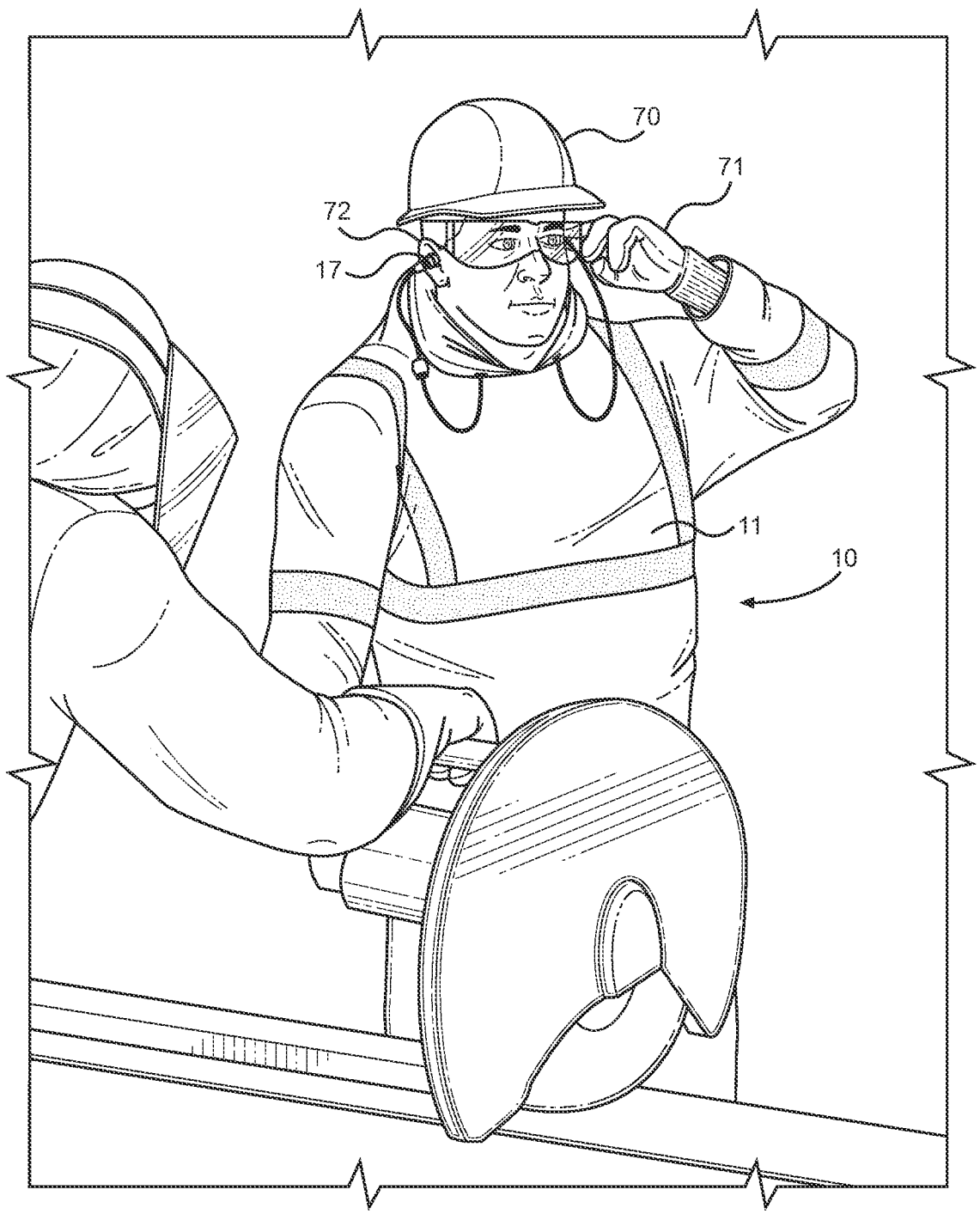
FIG. 4 shows a perspective view of an embodiment of the safety garment with integrated earplugs in use.

Referring now to FIG. 4, there is shown a perspective view of an embodiment of the safety garment with integrated earplugs in use. In operation, the user 70 will wear the safety garment with integrated earplugs 10 such that the garment 11 encloses the torso of the user 70. In the illustrated embodiment, the garment 11 includes a hood and sleeves to provide further protection for the user 70. Additionally, as is conventionally required in a construction or other, similar, workplace environments, the garment 11 includes reflective material disposed thereon to provide high-visibility to the user 70. A pair of earplugs 17 are affixed to a cord affixed to the garment 11. The user 70 is then able to use their hands 71 to secure each earplug 17 within each ear 72 when the ambient noise level requires it, thereby providing hearing protection. Additionally, the cord affixing the earplugs 17 to the garment 11 ensures that when the earplugs 17 are no longer required, the user 70 is able to easily remove the earplugs 17 without concern the earplugs 17 may be misplaced. In this way, the safety garment with integrated earplugs 10 provides a user with a single garment having both high visibility and hearing protection affixed thereto.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A safety garment with integrated earplugs, comprising:
a garment configured to encircle a user's torso;
wherein the garment is a vest;
wherein the garment includes a neck aperture along a top end configured to receive a head and neck therethrough;
a pair of arm apertures disposed on opposing sides of the garment;
wherein each of the pair of arm apertures is configured to receive an arm therethrough;
a reflective material disposed along a portion of an exterior surface of the garment; and
a cord affixed to the garment, the cord having a pair of opposing ends;
wherein an earplug is affixed to each end of the pair of opposing ends;
wherein the cord is affixed along a perimeter of the neck aperture through a plurality of loops, wherein each of the loops is aligned with one another;
wherein the garment is linearly split lengthwise along a central axis extending from the neck aperture to a bottom edge of the garment; and
wherein each earplug is removably affixed to one of the ends of the cord;
wherein the reflective material is disposed parallel to a bottom edge of the garment and positioned annularly about the torso; and
wherein the reflective material is additionally disposed parallel to each of the pair of arm apertures, such that the reflective material is positioned across each shoulder of the user and is adjoining the reflective material disposed around the torso.

2. The safety garment with integrated earplugs of claim 1, wherein the cord is dimensioned such that the earplugs attached thereto extend to the ears of the user.

3. The safety garment with integrated earplugs of claim 1, wherein the cord comprises a drawstring having a cord lock thereon.

4. The safety garment with integrated earplugs of claim 1, wherein each earplug is permanently affixed to an end of the cord.

5. The safety garment with integrated earplugs of claim 1, wherein the cord is composed of an elastic material.

* * * * *